United States Patent [19]

Sturm et al.

[11] Patent Number: 4,528,124

[45] Date of Patent: Jul. 9, 1985

[54] ALIPHATIC DICARBOXYLIC ACID ESTERS AS SCENTS

[75] Inventors: Wolfgang Sturm, Bevern; Gerd Mansfeld, Eschershausen; Hans Reindl, Bevern, all of Fed. Rep. of Germany

[73] Assignee: Haarmann & Reimer GmbH, Holzminden, Fed. Rep. of Germany

[21] Appl. No.: 518,869

[22] Filed: Aug. 1, 1983

[30] Foreign Application Priority Data

Aug. 5, 1982 [DE] Fed. Rep. of Germany ....... 3229300

[51] Int. Cl.[3] ............ A61K 7/46

[52] U.S. Cl. ............ 252/522 R

[58] Field of Search ............ 252/522 R

[56] References Cited

FOREIGN PATENT DOCUMENTS 1668564 2/1980 Fed. Rep. of Germany .
3229300 2/1984 Fed. Rep. of Germany .

OTHER PUBLICATIONS

Aretander, "Perfume and Flavor Chemicals", vol. I, (1969), #1058.

"Ullmanns Encyklopädie der Technischen Chemie"; vol. 11, 4th edition; Verlag Chemie, Weinheim/-Bergstr.; pp. 91–93.

"Chemical Abstracts", vol. 85, 1976, No. 117344m, p. 98.

*Primary Examiner*—Anton H. Sutto
*Attorney, Agent, or Firm*—Sprung, Horn, Kramer & Woods

[57] ABSTRACT

Aliphatic dicarboxylic acid esters of the formula $$R-O-\overset{\displaystyle O}{\overset{\|}{C}}-(CH_2)_n-\overset{\displaystyle O}{\overset{\|}{C}}-OR$$

in which

R denotes a methyl or isopropyl group and
n represents the number 9 or 10, are used as scents. They can be employed as components in perfume compositions and perfumed products.

12 Claims, No Drawings

ALIPHATIC DICARBOXYLIC ACID ESTERS AS SCENTS

The present invention relates to the use of aliphatic dicarboxylic acid esters as scents and to their use in perfume compositions and perfumed products.

Scents containing the aliphatic dicarboxylic acid esters of the formula $$R-O-\overset{\overset{\displaystyle O}{\|}}{C}-(CH_2)_n-\overset{\overset{\displaystyle O}{\|}}{C}-OR$$

in which

R denotes a methyl or isopropyl group and n represents the number 9 or 10, and, if appropriate, lower dicarboxylic acid esters, have been found.

The individual dicarboxylic acid esters are in some cases known (C.A., Vol. 85: 117,344 m; and DE-AS (German Published Specification) No. 1,668,564) and can be prepared from the corresponding acids or mixtures of acids by means of known esterification processes (Ullmanns Enzyklopädie der technischen Chemie [Ullmann's Encyclopaedia of Industrial Chemistry], 4th edition, Vol. 11, 91–93).

Preferred scents are mixtures of the dicarboxylic acid esters according to the invention and lower dicarboxylic acid esters. Lower dicarboxylic acid esters are essentially dimethyl and diisopropyl esters of decanedioic acid and of nonanedioic acid. If appropriate, the preferred scents also contain traces (less than 2% by weight, relative to the total mixture) of dicarboxylic acid esters having a fairly short chain. Examples of dicarboxylic acid esters having a shorter chain are the dimethyl and diisopropyl esters of hexanedioic acid (adipic acid), heptanedioic acid (pimelic acid) and octanedioic acid (suberic acid).

These preferred scents can be obtained if the mixture of dicarboxylic acids produced in the preparation of dodecanedioic acid by catalytic oxidation of cyclododecanol/cyclododecanone (DAS (German Published Specification) No. 1,668,564) is esterified with methanol or isopropanol.

Scents which are particularly preferred are those containing 30 to 50% by weight of dodecanedioic acid esters, 50 to 70% by weight of undecanedioic acid esters, 0.5 to 10% by weight of decanedioic acid esters and 0.5 to 5% by weight of nonanedioic acid esters as well as traces of lower dicarboxylic acid esters.

The scent of the scents according to the invention can be rendered by the following description of scents:

Dimethyl undecanedioate: warm, woody, powdery, resembling carrots and parsley.

Dimethyl dodecanedioate: agreeably resembling musk, like hot aldehyde, resembling blown-out candles, slightly woody.

Diisopropyl undecanedioate: warm, powdery, woody.

Diisopropyl dodecanedioate: resembling musk, warm, resembling blown-out candles, slightly woody.

The preferred scents are further distinguished by a note, particularly pronounced in the after-scent, of hot iron and blown-out candles; this note can be combined particularly effectively with other notes, such as aldehyde and bouquet notes.

The scents according to the invention can be used on their own or in mixtures with one another or in combination with other scents which are in themselves known (Arctander Perfume and Flavor Chemicals, Montclair, N.J. (USA), 1969).

The scents according to the invention can be combined with other scents to give perfume compositions having expressive notes.

As well as their excellent scent properties, the aliphatic dicarboxylic esters according to the invention have an excellent fixing property and also a high degree of stability and are therefore excellently suitable, inter alia, for use as scents for finished products in the field of cosmetics, fine perfumes, aerosols, detergents and, in particular, industrial chemistry, for example for washing agents, hair tonic agents, foam baths, bath salts, dishwashing agents, machine dishwashing agents, shampoos, fabric softener rinses, washing powders, soaps, anti-perspirants, powders, creams, shaving lotions, after-shave lotions, room fresheners, toilet cleansers, room sprays anti-perspirant sprays, deodorant sprays, body sprays, insecticide sprays and sunscreen compositions.

In general, the scents according to the invention are employed in these formulations in an amount of 0.001 to 10% by weight, preferably 0.01 to 10% by weight, relative to the finished formulation.

These perfumed products are prepared in a customary manner.

EXAMPLE 1

Preparation of a perfume oil:

A perfume oil is prepared in accordance with the following formulation (composition in parts by weight):

20 parts of styryl acetate,
50 parts of iraldein,
100 parts of phenylethyl alcohol,
72 parts of p-tert.-butylcyclohexyl acetate,
50 parts of cinnamyl alcohol,
30 parts of patchouli oil,
3 parts of galbanum resin,
70 parts of 4-(4-hydroxy-4-methylpentyl)-3-cyclohexene- 1-carboxaldehyde,
50 parts of α-hexylcinnamaldehyde,
5 parts of undecylenealdehyde,
30 parts of benzyl acetate,
20 parts of dimethylbenzylcarbinol acetate and
50 parts of methyl abietate.

EXAMPLE 2

Portions of 50 parts by weight of the following dicarboxylic acid esters are added to separate samples of the perfume oil prepared in accordance with Example 1:

(a) dimethyl undecanedioate,
(b) dimethyl dodecanedioate,
(c) diisopropyl undecanedioate,
(d) diisopropyl dodecanedioate and
(e) a mixture of 32 parts by weight of dimethyl dodecanedioate, 58 parts by weight of dimethyl undecanedioate, 8 parts by weight of dimethyl decanedioate and 2 parts by weight of dimethyl nonanedioate and also traces of lower dioic acid esters.

The result of adding the scents (a) to (e) was to impart a fuller scent and considerably greater harmony to the perfume composition. The flower notes were rendered more strongly and the wood notes became more powdery and warmer. In addition, an increased effulgence was imparted to the compositions.

What is claimed is:

1. A scenting composition comprising a base and a scenting amount of at least one aliphatic dicarboxylic acid ester of the formula $$R-O-\overset{\overset{O}{\|}}{C}-(CH_2)_n-\overset{\overset{O}{\|}}{C}-OR$$

in which
R is a methyl or isopropyl group, and
n is 9 or 10.

2. A composition according to claim 1, further containing about 0.5 to 10% by weight of at least one ester of decanedioic acid and about 0.5 to 5% by weight of at least one ester of nonanedioic acid, percentages being based on the combined weights of said aliphatic dicarboxylic acid ester, decanedioic acid ester and nonanedioic acid ester.

3. A composition according to claim 2, wherein esters wherein n is 10 are present in about 30 to 50% by weight and the esters wherein n is 9 are present in about 50 to 70% by weight.

4. A composition according to claim 3, further containing a trace of esters of dioic acids of shorter chain length.

5. In the scenting of products for personal or home care wherein a scenting composition is combined with a personal or home care base, the improvement wherein said composition includes at least one aliphatic dicarboxylic acid ester of the formula $$R-O-\overset{\overset{O}{\|}}{C}-(CH_2)_n-\overset{\overset{O}{\|}}{C}-OR$$

in which
R is a methyl or isopropyl group, and
n is 9 or 10.

6. The process according to claim 5, wherein the aliphatic dicarboxylic acid esters are present in about 0.001 to 10% by weight of the product.

7. The process according to claim 6, wherein esters wherein n is 10 are present in about 30 to 50% by weight and the esters wherein n is 9 are present in about 50 to 70% by weight, the scenting composition further containing about 0.5 to 10% by weight of at least one ester of decanedioic acid and about 0.5 to 5% by weight of at least one ester of nonanedioic acid, percentages being based on the combined weights of said aliphatic dicarboxylic acid ester, decanedioic acid ester and nonanedioic acid ester.

8. A perfume or perfumed product comprising a base and at least one aliphatic dicarboxylic acid ester of the formula $$R-O-\overset{\overset{O}{\|}}{C}-(CH_2)_n-\overset{\overset{O}{\|}}{C}-OR$$

in which
R is a methyl or isopropyl group, and
n is 9 or 10.

9. A composition according to claim 8, wherein the aliphatic dicarboxylic acid esters are present in about 0.001 to 10% by weight.

10. A composition according to claim 8, wherein esters wherein n is 10 are present in about 30 59 50% by weight and the esters wherein n is 9 are present in about 50 to 70% by weight, wherein n is 9 are present in about 50 to 70% by weight, the scenting composition further containing about 0.5 to 10% by weight of at least one ester of decanedioic acid about 0.-to 5% by weight of at least one ester of nonanedioic acid, percentages being based on the combined weights of said aliphatic dicarboxylic acid ester, decanedioic acid ester and nonanedioic acid ester.

11. A composition comprising about 30 to 50 parts by weight of an aliphatic dicarboxylic acid ester of the formula $$R-O-\overset{\overset{O}{\|}}{C}-(CH_2)_{10}-\overset{\overset{O}{\|}}{C}-O-R$$

in which
R is a methyl or isopropyl group,
and about 50 to 70 parts by weight of an aliphatic dicarboxylic acid ester of the formula $$R-O-\overset{\overset{O}{\|}}{C}-(CH_2)_9-\overset{\overset{O}{\|}}{C}-O-R.$$

12. A composition according to claim 11, further containing about 0.5 to 10 parts by weight of at least one ester of decanedioic acid and about 0.5 to 5 parts by weight of at least one ester of nonanedioic acid.

* * * * *